(12) United States Patent
Shimizu et al.

(10) Patent No.: US 6,662,113 B1
(45) Date of Patent: Dec. 9, 2003

(54) DIGITAL CORRELATION OF TEST SAMPLES AND THE SCREENING OF INTERACTIONS BETWEEN THE SAME

(75) Inventors: Nobuyoshi Shimizu, Sakura (JP); Shuichi Asakawa, Tokyo (JP)

(73) Assignee: Fujisawa Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 09/355,944

(22) PCT Filed: Dec. 15, 1998

(86) PCT No.: PCT/JP98/05661
§ 371 (c)(1),
(2), (4) Date: Nov. 23, 1999

(87) PCT Pub. No.: WO99/31270
PCT Pub. Date: Jun. 24, 1999

(30) Foreign Application Priority Data

Dec. 15, 1997 (JP) .............................................. 9/345441
Apr. 1, 1998 (JP) .............................................. 10/88571

(51) Int. Cl.[7] .............................. C12Q 1/00; C12Q 1/68; G01N 33/543; G01N 33/551; G01N 33/553; G01N 33/552; G01N 33/544; G01N 33/48
(52) U.S. Cl. ................................ 702/19; 435/4; 435/6; 436/518; 436/524; 436/525; 436/526; 436/527; 436/528; 702/19; 702/20
(58) Field of Search .............................. 435/6, 4, 518, 435/524, 525, 526, 527, 528; 702/19, 20

(56) References Cited

U.S. PATENT DOCUMENTS 5,622,823 A * 4/1997 Perlin .............................. 435/6
6,027,880 A * 2/2000 Cronin .......................... 435/6

FOREIGN PATENT DOCUMENTS

WO WO-87/01374 * 3/1987
WO WO-97/20931 * 6/1997

OTHER PUBLICATIONS

Diaz and Garcia, Instruction of a broad–host–range pneumococcal promoter–probe plasmid; Gene, vol. 90, No. 1, 1990 Elsevier Science Publishers B.V. (Biomedical Division).*

Asakawa S et al, "High–fidelity digital hybridization screening", Genomics, Apr. 15, 1998, vol. 49, No. 2, pp. 209–217.*

S. Asakawa, et al., 43rd Annual Meeting of Japanese Society of Human Genetics, pp. 139, 1998.

* cited by examiner

*Primary Examiner*—John S. Brusca
*Assistant Examiner*—Shubo "Joe" Zhou
(74) *Attorney, Agent, or Firm*—Oblon, Spivak, McClelland, Maier & Neustadt, P.C.

(57) ABSTRACT

A method for determining the physical, chemical, or biological correlation between test samples in group A and test samples in group B. This correlation can be determined by contacting a mixture of test samples selected according to a certain rule from group A with test samples from group B to detect the interaction(s) between them. The number of reactions needed to detect these interaction(s) is greatly reduced by preparing a mixture of test samples in group A according to the principle of binary notation, and thus enables a rapid screening.

17 Claims, 1 Drawing Sheet

DIGITAL CORRELATION OF TEST SAMPLES AND THE SCREENING OF INTERACTIONS BETWEEN THE SAME

TECHNICAL FIELD

The present invention relates to a method for efficiently screening an enormous number of test samples. More specifically, it relates to a method for efficiently detecting the correlation between test samples in groups A and B when they have material interactions between them. For example, the method of the present invention is especially useful for genomic structural analysis.

BACKGROUND ART

Research on genomic structural analysis these days can be classified as "genome mapping" and "sequencing." In genome mapping, the chromosomal DNA structure is reconstructed by mapping the genome using various techniques and by aligning many fragmented genomic DNAs. In sequencing, the nucleotide sequence of genomic DNA is clarified by determining nucleotide sequences of aligned DNA fragments. The present invention is especially useful for genome mapping.

Previously, when test samples in groups A and B materially interacted, detecting their correlation required examining whether or not each test sample successively withdrawn one-by-one from group A corresponded to each test sample in group B in the interaction. Therefore, if group A consists of m samples and Group B consists of n test samples, (m)×(n) screenings were required.

An example of such a conventional screening method is the method for correlating Sequence Tagged Site (STS) markers (group A) with Bacterial Artificial Chromosome (BAC) clones (group B). STS is a concept for systematically marking the human genome (Olson, M. et al., Science 245: 1434–1435, 1989). STSs consist of short nucleotide sequences of about 200 to 300 bp and possess a sequence which cannot be found in other sites of the genome. Accordingly, the same STS contained in multiple clones indicates that these clones share common regions. By performing PCR using primers designed for STS with genomic DNA as the template, the amplified product of a length corresponding to the STS can be confirmed as a single band (S. B. Primrose, "Principles of Genome Analysis" Blackwell Science Ltd., 1995). In the combination of STS markers (group A) and BAC clones (group B), a BAC clone corresponding to an STS marker is used to be detected by a method based on PCR screening or hybridization screening STS markers one-by-one and BAC clones.

Physical mapping using STS has been used in a limited field by many researchers. The region of the causative gene for cystic fibrosis covered by 30 YAC clones in chromosome 7 has been integrated into a single aligned clone of more than 1.5 Mb (Green & Olson, Science 250: 94–98, 1990). Foote et al. succeeded in aligning 196 clones covering more than 98% of the euchromatin region of the human Y chromosome (Foote et al., Science 258: 60–66, 1992). A YAC-STS integrated map, a combination of physical map with genetic map, on the long arm (q) of chromosome 21 has been prepared (Chumakov et al., Nature 359, 380–387, 1991).

These days, a combination of BAC libraries or PAC (P1-derived artificial chromosome) libraries with STS markers enables covering most human genome. However, a method for efficiently detecting numerous correspondences of STSs to such large-scale libraries has not been established.

In these conventional methods, the increasing number of test samples in groups A and B results in a geometrically progressive increase in the number of screenings, requiring enormous amounts of time and labor.

For example, in genome mapping in general, screening of DNA libraries usually requires numerous repetitions of filter hybridizations or a series of PCR assays of prepared for each library(Asakawa et al., Gene 191: 69–79, 1997). Therefore, to align library clones covering the entire human genome, numerous combinations of DNA libraries and probes must be screened.

The utilization of DNA chips for genomic analysis is highly expected to facilitate more speedy screening. Since oligonucleotides of desired nucleotide sequences can be cumulated in high density on DNA chips, the hybridization assay can be carried out for numerous combinations by a single hybridization. In fact, the mapping of 256 varieties of STS markers against yeast cosmid clone using DNA chips has been reported (Sapolsky, R. J. et al., Genomics 33, 445–456, 1996). However, according to the conventional approach to these problems, the correlation must be examined for all probable combinations of DNAs and probes as before, even with DNA chips. The utilization of DNA chips as such thus does not provide a novel principle enabling the efficient detection of correlation for numerous combinations.

DISCLOSURE OF THE INVENTION

The present inventors considered that the utilization of mixed test samples might reduce the work for detecting the interaction between test samples. Naturally, the random mixing of test samples is not useful for the final clarification of correlation based on their interactions. By systematically mixing test samples in group A based on binary notation and identifying the interactions between this mixture and test samples in group B, the present inventors have found that the correlation between the groups can be more efficiently, identified than prior methods accomplishing this invention.

An objective of this invention is to efficiently detect the correlation by the following method, when test samples (Ai) in group A correlate to test samples (Bj) in group B based on material interactions. Namely, the present invention relates to the following method:

The "k" in the phrase "the k-th bit" is the integer at the "k" position in the numbering of a bit starting from the right of the figure. For example, the k-th bit of "110" where k equals 1 is "0".

[1] a method for determining a combination of test samples out of those constituting groups A and B which correlate physically, chemically or biologically, wherein said method comprises the following steps:

(1) providing m ($2^{n-1}$=<m=<$2^n$-1 where m and n are natural numbers;, m>=3, n>=2) test samples Ai (3=<i= <m) in group A and x (x is a natural number) test samples Bj (1=<j=<x) in group B, (2) assigning a g-bit (n=<g) ID number based on the binary notation to each test sample Ai in group A, (3) mixing test samples Ai in group A having "1" for the first bit of ID numbers based on binary notation to make mixture C1, and similarly mixing test samples Ai in group A having "1" for the k-th (1=<k=<g) bit of ID numbers to make mixture Ck, thus obtaining g-varieties of mixtures comprising mixtures from C1 through Cg, (4) detecting the interaction of each of g varieties of mixtures from C1 through Cg with test samples Bj in group B, (5) determining g-bit binary numbers having "1" or "0" for the k-th bit by assigning "1" when the interaction is detected between each mixture constituting mixtures from C1 through Cg and Bj in group B, and "0" when no interaction is detected, and (6) determining the correlation between test sample Ai in group A and test sample Bj in group B by referring test sample Ai in group A to the corresponding binary number obtained; (5)

[2] the method of [1], wherein the correlation between test samples involves the interaction between test samples constituting group A and group B;

[3] the method of [2], wherein the correlation based on the interaction between test samples is in the ratio of 1:1 or 1:many;

[4] the method of [1], wherein g is n;

[5] the method of [4], wherein each test samples in group A is assigned an individual ID numbers up to $2^n1$ to test samples;

[6] the method of any one of [1] through [5], wherein said method comprises steps for detecting the interaction between mixture Ca obtained by mixing all test samples in group A and test sample Bj in group B;

[7] a method for determining a combination of test samples out of those constituting groups A and B and correlating them physically, chemically or biologically, wherein said method comprises assigning ID numbers of more than two series to one test sample in group A followed by the repetition of the method of [1];

[8] the method of any one of [1] through [7], wherein said test sample in group A is an oligonucleotide and said test sample in group B is DNA; and

[9] an STS mapping method comprising performing the method of [8], wherein said method uses STS markers as test samples in group A and genome libraries as test samples in group B.

The principle of the present invention is as follows.

(1) First, "m" ($2^{n-1}$=<m=<$2^n$−1 where m and n are natural numbers; m>=3, n>=2) test samples Ai (3=<i=<m) in group A and "x" (x is a natural number) test samples Bj (1=<j=<x) in group B are provided, and (2) each test sample Ai in group A is assigned a number based on binary notation.

An ID number is systematically assigned by converting the number based on decimal notation to binary notation as shown in Table 1 (wherein p, q, r, P, Q, and R are "0" or "1"). In order to assign each test sample an individual number based on the binary notation, $2^n$31 1 numbers with n-bit are required. In the following, the number assigned to each test sample in group A may be referred to as the ID number.

TABLE 1

| Test sample in group A | Individual decimal number | Individual n-bit binary number |
|---|---|---|
| A1 | 1 | **001 |
| A2 | 2 | **010 |
| * | * | ***** |
| Ai | i | **pqr ( . . . 4p + 2q + r = i) |
| * | * | ***** |
| Am | m | **PQR( . . . 4P + 2Q + R = m) |

The mixtures are then prepared by mixing test samples in group A according to the following procedure (3).

(3) Test samples Ai in group A having "1" for the first bit of the ID number based on binary notation are mixed to make mixture C1. Similarly, test samples Ai in group A having "1" for the k-th bit of ID numbers are mixed to make mixture Ck (1=<k=<n) so that n different mixtures from C1 through Cn are obtained.

The criteria for preparing this mixture are shown in Table 2, wherein Cn–C1 represent mixtures, and "1" indicates the addition of each test sample in group A to each mixture, and "0" indicates no addition.

TABLE 2

| Test sample in group A | Cn | C... | Ck | ... | C3 | C2 | C1 |
|---|---|---|---|---|---|---|---|
| A1 | ... | ... | ... | ... | 0 | 0 | 1 |
| A2 | ... | ... | ... | ... | 0 | 1 | 0 |
| ... | ... | ... | ... | ... | ... | ... | ... |
| Ai | ... | ... | ... | ... | p | q | r |
| ... | ... | ... | ... | ... | ... | ... | ... |
| Am | ... | ... | ... | ... | P | Q | R |

By utilizing mixtures thus obtained and performing procedures (4) to (5) below, the binary numbers by which test samples in group A are specified are determined.

(4) With each of these n-varieties of mixtures from C1 through Cn, the interaction of test samples Bj in group B is detected, and (5) With each mixture Ck constituting mixtures from C1 through Cn, Ck is assigned "1" when the interaction of test sample Bj in group B is detected, and "0" when the interaction is not detected, thus determining an n-bit binary number having "0" or "1" for the k-th bit.

Procedures for determining the binary numbers are summarized in Table 3. In this table, the presence of interaction of mixtures Cn–C1 in each of the test samples constituting group B is indicated as "1," and the absence, as "0." Based on this table, the k-th bit represents the detection result of the interaction of each test sample mixture Ck in group A with a specific test sample in group B.

TABLE 3

| Test sample in group B | Cn | C... | Ck | ... | C3 | C2 | C1 | Test sample in group A |
|---|---|---|---|---|---|---|---|---|
| B1 | ... | ... | ... ... | ... | ... | ... ... | ... | |
| B2 | ... | ... | ... ... | ... | ... | ... ... | ... | |
| ... | ... | ... | ... ... | ... | 0 | 0 | 1 | A1 |
| Bj | ... | ... | ... ... | ... | s | t | u | A . . . 4s + 2t + u |
| ... | ... | ... | ... ... | ... | 0 | 1 | 0 | A2 |
| Bx | ... | ... | ... ... | ... | S | T | U | A . . . 4S + 2T + U |

Finally, procedure (6) determines the test sample in group A corresponding to a specific test sample in group B.

(6) The correlation between test sample Ai in group A and test sample Bj in group B is determined by referring to the test sample Ai in group A which corresponds to the binary number obtained in (5).

In the present invention, the physical, chemical or biological correlation between test samples constituting groups A and B means the relationship by which test samples in both groups interact as mediated by the physical, chemical or biological reaction. Preferably, this reaction is specific so that it can be detected only between specific test samples. Also, the correlation in interactions between test samples in group A and those in group B means that test samples in group A and those in group B are somehow correlated so that their relationship can be clarified by detecting their interaction. For example, interactions between test samples can be represented by the binding reaction based on the specific affinity. More specifically, the binding reaction is exemplified by hybridization of nucleic acid, antigen-antibody reaction, various ligand-receptor reactions, or enzyme-substrate reactions.

Figure 1:
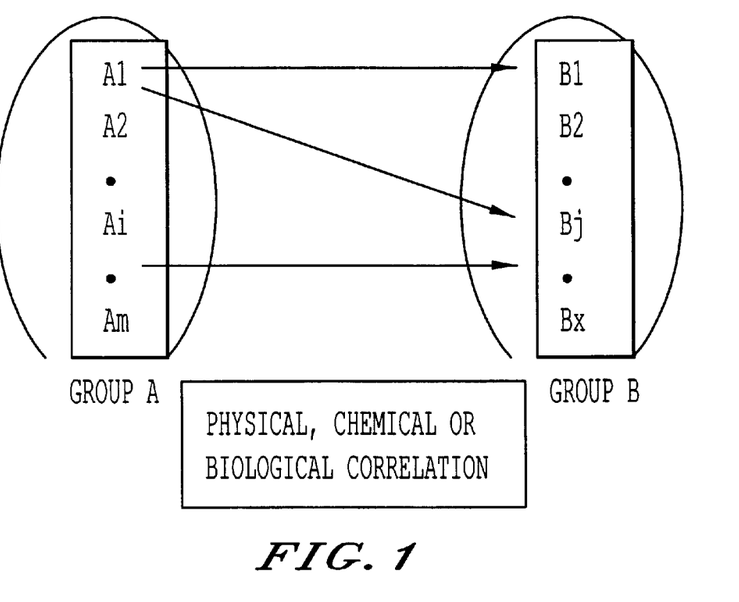
FIG. 1 depicts the correlation model of test samples in group A with those in group B.

In addition, the interaction can be not only the binding reaction between materials but also the functional combination associated with the signal transduction. The functional combination can be exemplified by the combination triggering the transcriptional initiation or signal transduction associated with the binding of the transcriptional regulatory factor to the transcriptional regulatory region, or the binding of the agonist compound to the membrane receptor. In the present invention, the correlation between test samples in both groups is not limited to 1:1, and can be 1:many as shown in FIG. 1. Preferably, in this invention, the correlation of test samples in group A with those in group B is as close to 1:many or 1:1 as possible. However, the correlation can be accurately detected even in a many:1 relation, for example according to the method described below utilizing this invention.

The method of the present invention can be applied to any combination if the interaction between test samples (Ai) in group A and test samples (Bj) in group B can be detected. However, since it is necessary to use mixtures of test samples in group A, the failure to detect the interaction with test samples in group B owing to mixing of test samples belonging to group A should be avoided. The present invention can be utilized when the correlation between two groups must be detected. More preferably, the correlation can be detected based on the interaction between materials. This invention is especially useful for assaying numerous test samples such as in genomic analysis, high throughput screening, combinatorial chemistry, or etc.

For example, group A can be oligonucleotide markers (such as STS markers, VNTR, RFLP, or microsatellite), and group B, DNA library clones (genomic library clones such as BAC, PAC, P1, YAC, cosmid vectors or etc.). This invention may thus be used for the binding assay for a gene using numerous transcriptional regulatory factors and analogues thereof, proteins and binding proteins, antigens and antibodies, enzymes and substrates, etc. Furthermore, this invention can be used for mapping cDNA and EST to genome. In particular, genome mapping, wherein numerous repetitions of screening are required and the desirable correlation between test samples in two groups (that is, 1:1, or 1:many) can be expected, is a useful field of application of the invention. The present inventors have designated the method of using this invention in genome analyses as "digital hybridization screening."

When there are three or more test samples (m) in group A, the use of this invention can reduce the number of screenings as compared with identifying the interactions with all combinations of test samples. For example, when m is three, the number of screenings (n) becomes two; when m is seven, n becomes three; and when m is 123, n becomes seven ($2^{n-1}$=<m=<$2^n$-1; m and n are natural numbers, m>=3, n>=2). According to the present invention, seven repeated confirmations of interaction will thus give the same results as by confirming interactions with each of the 123 test samples. In this invention, screening efficiency increases with the number of test samples in group A.

In addition, if the possibility that test samples constituting group B will definitely correspond to any of the test samples in group A is previously guaranteed, there is theoretically an exceptional relation between m and n. In such a situation, all negative values (e.g., 00000000) can be corresponded.

Therefore, m and n are related as $2^{n-1}+1$=<m=<$2^n$ where m and n are natural numbers and m>=3, n>=2.

However, in some cases, having too many test samples in group A will decrease the sensitivity for detecting the correlation between test samples. The decreased sensitivity can be avoided by performing the present invention after dividing test samples in group A into appropriate subgroups. In some other cases, an increasing number of test samples in group A will increase the possibility that the correlation becomes "many:1." Increasing the correlation of "many:1" may reduce the accuracy of detecting correlation. A high possibility for a correlation of "many:1" may occur when DNA markers that are assumed to be very closely localized to the test sample in group A are used and the test sample in group B is a DNA library such as BAC clones. In such a case, DNA markers constituting group A are first collected in one group. The present invention is then applied with this group thus formed as one of the test samples in group A. Collecting test samples into one group means assigning the same ID number to different test samples in group A. BAC clones which are clearly not correlated should be selected out at this stage and further subjected to a secondary screening by an appropriate method. Alternatively, for analogues of chemical compounds, screening should be performed with a group of analogues as one test sample then subjecting the analogues to a secondary screening by a suitable method. The secondary screening can be performed by individually identifying the mutual relations between test samples. For example, in order to detect the mutual relations between BAC clones and STS by secondary screening, hybridization using individual probes or PCR using STS primers with the BAC clone as the template is performed to determine the correlation.

There are, however, no particular limitations in the number of test samples (x) in group B; the efficiency increases with increasing the number (x).

The number assigned to each test sample Ai in group A can be made an ID specific to the sample by selecting a suitable number up to $2^n$-1. In general, the ID number should be unique to each test sample. However, as described above, it is also possible to collectively give the same ID number to different test samples as one group. When there are close to $2^{n-1}$ test samples, preferably the ID numbers may be assigned randomly instead of assigning numbers sequentially from 1 so that numbers are properly distributed among test samples. Also, preferably the difference in the number of test samples Ai in group A contained in each mixture Ck may be minimized. For example, if Ai comprises 64 test samples, only A64 (1000000) has "1" for the seventh bit of the ID number when numbers are assigned sequentially from 1. Therefore, each mixtures from C1 up to C6 comprises 32 test samples, whereas mixture C7 contain only one test sample, A64 (1000000). This situation does not substantially affect the digital hybridization screening at all. However, equalizing the numbers of test samples comprising each mixture Ck can be expected to standardize the labeling and to make the background level uniform. More specifically, it is possible to make the difference in the number of test samples comprising each mixture Ck one or less. Even in the case of 64 test samples above, it is possible to make the difference in the number of test samples in each mixture 1 by assigning successive numbers from the 32nd to 95th based on decimal notation (from 0100000 to 1011111 in binary notation). By other numbering, it is also possible to distribute 64 test samples among mixtures wherein the difference in the number of test samples in each mixture is one or less.

In the present invention, test sample Ai in group A is assigned an ID number based on the binary notation and used for to prepare mixture Ck. By using the binary notation, the results of interaction detection can be directly correlated with the numeral for each bit. In binary notation, a number is generally written with "1" and "0". However, in the present invention, a binary number can be expressed with symbols other than "1" and "0" since "1" or "0" indicates the presence or absence of a bit in binary notation and does not limit the invention to using only "1" or "0."

In preparing mixture Ck (1=<k=<n) which comprises test samples "Ai"s in group A, the amount of test sample Ai in group A comprising each mixture is not particularly limited. In some cases, for example, mixing Ai in an equal amount or an equimolar amount produces a homogeneous rate of interaction with test samples in group B, facilitating the easy interpretation of detection results. If there is a difference in the labeling efficiency among respective "Ai"s or in the rate of interaction between groups A and B owing to the combination, it is possible to equalize the rate of interaction by modulating the ratio of "Ai"s. For example, the present invention can use a mixture of probes comprising radioisotope-labeling DNA by two different methods, the kination method and the random oligomer elongation method. In such a case, since the intensity of signals obtained from each probe is expected to be different, an equalized signal intensity cannot be achieved by an equal amount mixing. Therefore, we can attempt to equalize the signal intensity by first measuring the labeling efficiency and signal intensity of each probe, and, based on the result, adjusting the mixing ratio of probes.

In the present invention, drugs and solvents which do not adversely affect screening may be added to mixture Ck, in addition to test samples "Ai"s in group A. If the test sample in group A may adversely affect the screening by interaction, an agent may be added to reduce the harmful effect.

Mixture Ca comprising all test samples in group A may be used to enhance the fidelity of the present invention. If results showing the interaction are not obtained due to the reaction between Ca and test samples in group B, either there is no combination which causes an interaction between them or there is a problem in detecting the interaction.

The interactions of n varieties of mixtures from C1 through Cn with each of test samples Bj in group B can be detected by any methods for identifying their interaction. For example, interactions between oligonucleotides and DNAs can be detected using hybridization between them as the marker.

In order to describe the present invention more understandably, a hypothetical screening of 24 clones as group B performed with six DNA markers as group A is diagrammatically represented here. These six DNA marker probes were specified by assigning a three-bit ID number to each probe, for example, "001" to DNA probe 1 and "010" to DNA probe 2 (Table 4).

TABLE 4

|  | M3 | M2 | M1 | ID number | MA |
|---|---|---|---|---|---|
| DNA probe 1 | 0 | 0 | 1 | 001 | 1 |
| DNA probe 2 | 0 | 1 | 0 | 010 | 1 |
| DNA probe 3 | 0 | 1 | 1 | 011 | 1 |
| DNA probe 4 | 1 | 0 | 0 | 100 | 1 |
| DNA probe 5 | 1 | 0 | 1 | 101 | 1 |
| DNA probe 6 | 1 | 1 | 0 | 110 | 1 |

Figure 2:
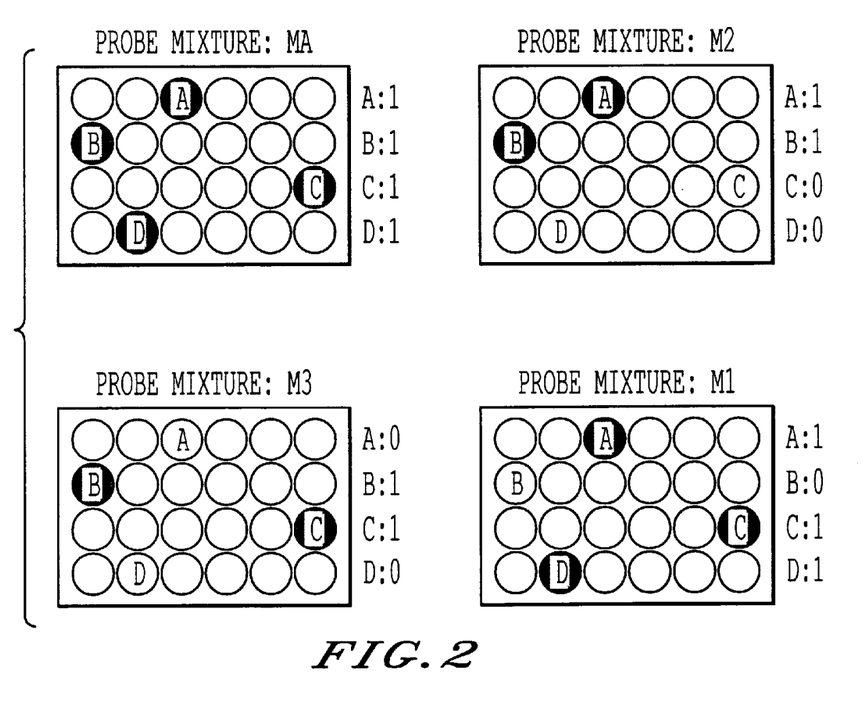
FIG. 2 depicts the hybridization pattern model when the screening method of the present invention was performed using six DNA markers (group A) and 24 clones (group B). Four DNA probe mixtures (M, M1, M2, and M3) were provided, and each probe mixture was separately hybridized with four identical replica filters containing 24 clones each. The probe mixture MA, containing all six probes, detected four clones (A, B, C, and D), whereas other probe mixtures detected these same clones in different combinations.

These DNA probes were then mixed in the combinations shown in Table 4 to prepare four probe mixtures, M1, M2, M3, and MA. In the table, "1" indicates the presence of the marker and "0" indicates its absence. Four probe mixtures (MA, M1, M2, and M3) were provided, and hybridization was carried out separately with each of these probe mixtures against four identical clone filters (FIG. 2). The probe mixture MA, containing all six probes, detected four clones (A, B, C, and D), whereas other probe mixtures detected these same clones in different combinations. The hybridization pattern was then examined for individual clones, for example, clone A was positive for probe mixtures M1 and M2 but negative for M3, resulting in the three-bit pattern "011". This matrix pattern indicated that clone A is correlated with a specific DNA probe 3 (Table 5). Similarly, the remaining three clones were correlated with specific DNA probes.

TABLE 5

| Clone | M3 | M2 | M1 | Determined DNA probe |
|---|---|---|---|---|
| Clone A | 0 | 1 | 1 | DNA probe 3 |
| Clone B | 1 | 1 | 0 | DNA probe 6 |
| Clone C | 1 | 0 | 1 | DNA probe 5 |
| Clone D | 0 | 0 | 1 | DNA probe 1 |

In DNA library screening using DNA probes, screening fidelity can be enhanced as follows.

(1) Use double-offset filters or two replica filters for a single series of probe mixtures to prevent erroneous results caused by false-positive and false-negative signals. These filters are all to yield the same detection results as the original filter. Accordingly, they must generate identical signal patterns for the same series of probe mixtures. Any difference in the signal detection pattern indicates that either of results is erroneous.

(2) Adding a parity bit to each ID number will standardize the number of "1" based on binary notation to an even number (Table 6). That is, test samples of group A having an odd number of "1" constituting the ID number are collected to provide mixture Co, and signals from test samples in group B for this mixture are simply recorded. When an interaction between test samples in group B and this mixture Co is detected, a parity bit of "1" is added to the ID number. When a test sample in group B which interact with test samples in group A originally have an even number of "1" in the ID number, the interaction is not to be detected with said mixture Co, therefore the parity bit is always 0. As a result, the number of 1's in the ID number+parity bit is always an even number with all test samples in group B. One bit for the parity bit is added to seven-bit figures to determine the ID number obtained through the above-described procedures, and the resulting eight-bit figures are referred to as test samples in group A.

TABLE 6

In this table, the sum of "1" in ID bit + parity bit is made an even number.

|  | ID bit | Parity bit | Number of "1" |
|---|---|---|---|
| STS1 | 0000001 | 1 | 2 |
| STS2 | 0000010 | 1 | 2 |
| STS3 | 0000011 | 0 | 2 |
| STS4 | 0000100 | 1 | 2 |
| STS5 | 0000101 | 0 | 2 |
| STS6 | 0000110 | 0 | 2 |

TABLE 6-continued

In this table, the sum of "1" in ID bit + parity bit is made an even number.

| | ID bit | Parity bit | Number of "1" |
|---|---|---|---|
| STS7 | 0000111 | 1 | 4 |
| . | . | . | . |
| . | . | . | . |
| . | . | . | . |
| STS80 | 1011010 | 0 | 4 |
| STS81 | 1011011 | 1 | 6 |
| . | . | . | . |
| . | . | . | . |
| . | . | . | . |
| STS126 | 1111110 | 0 | 6 |

The "1" in the finally decided eight-bit figures are counted. If a signal is missing or excessive for any bit, the number of "1" will become an odd number, indicating trouble. A hypothetical case in which the number of "1" constituting the ID bit and parity bit is standardized to an even number is described. Obviously, the number of bits can also be standardized to an odd number. When standardized to an odd number, an even number of "1" indicates trouble. Thus, the fidelity of the screening method in the present invention can be enhanced by using only one additional series of filter.

(3) Performing another screening with a reverse bit assigned to each ID of an STS will also remarkably enhance the fidelity of the screening method of the present invention (Table 7).

TABLE 7

| | Screening 1 | Screening 2 |
|---|---|---|
| STS1 | 0000001 | 1111110 |
| STS2 | 0000010 | 1111101 |
| STS3 | 0000011 | 1111100 |
| STS4 | 0000100 | 1111011 |
| STS5 | 0000101 | 1111010 |
| STS6 | 0000110 | 1111001 |
| STS7 | 0000111 | 1111000 |
| . | . | . |
| . | . | . |
| . | . | . |
| STS80 | 1011010 | 0100101 |
| STS81 | 1011011 | 0100100 |
| . | . | . |
| . | . | . |
| . | . | . |
| STS126 | 1111110 | 0000001 |

If the screening result is precise, ID (screening 1) plus ID (screening 2) is always 1111111. If any signals are missing, ID (screening 1) plus ID (screening 2) is always <1111111. If more than one STS hybridizes with a single clone, ID (screening 1) plus ID (screening 2) is always >1111111. This strategy requires two screenings.

Therefore, the maximum advantage of performing screenings 1 and 2 is that a combination of probe and clone in an accurate correlation can be detected. In contrast, with the result obtained by either screening 1 or screening 2 alone, it is impossible to discriminate correct cases, incorrect cases, and cases in which more than one probe hybridizes with a single clone, resulting in mixed data in these cases. If most results of either screening are correct, two screenings are not required. However, in general, two screenings provide a significant capability to distinguish the correct result from the incorrect ones.

Performing two screenings enables not only enhancing the fidelity of screening but also separating multiple signals caused by the many:1 correspondence. The separation of signals will be specifically described in the following. For example, a single STS probe is assigned binary ID numbers in two different series, FORWARD ID and REVERSE ID. FORWARD ID and REVERSE ID are assigned binary numbers in an independent series, and mixtures in different combinations are prepared. The correlation with clones constituting libraries will be determined separately based on the present invention. In such an embodiment with FORWARD ID and REVERSE ID, the following natural number relation is independently established:

$$2^{n-1} = <m = <2^n - 1,$$

where m and n are natural numbers, m>=3, and n>=2.

FORWARD ID and REVERSE ID for a single STS probe are assigned so that their sum always has "1" in all bits. When one probe corresponds to a certain clone, the sum of FORWARD ID and REVERSE ID determined for that clone must thus have "1" in all bits. For example, in eight-bit IDs, the sum will become "11111111." However, when two STS probes hybridize with one particular clone, the sum of FORWARD ID and REVERSE ID derived from the hybridization contains "2" for more than one bit such as "11221212" for an eight-bit number. The addition here does not follow binary notation, but, for convenience's sake, follows the notation 1+1=2, 0+1=1, 1+0=1, and 0+0=0 for each bit, because this is more easily understood than binary notation. However, this invention is not limited to such an expression pattern. The expression pattern need only clearly indicate whether both FORWARD ID and REVERSE ID, only one of them, or neither of them are obtained for each bit. In such a case, it is possible to deduce which two of the STS probes hybridize with a clone according to the following concept. The presence of "2's" in only one place, that is, the expression of "2" for only 1 bit as in "11121111," indicates the interaction with one combination of STS probes (two probes), enabling the straight forward identification of both STS probes.

Theoretically, as the number of bits containing "2" increases to 2, 3, 4, 5, 6, 7, or 8, the number of STS probes corresponding to the target increases to 4, 8, 16, 32, 64, 128, or 254 and there are thus 2, 4, 8, 16, 32, 64, or 127 different combinations of probe pairs corresponding to the target. That is, when "2" are expressed in 2, 3, 4, and 5 bits, the possible correspondence of STS probes can be narrowed to 4, 8, 16, and 32 varieties (half of the combinations). If one or two probes correspond to one particular clone, their correlation can be narrowed in this way.

When screenings 1 and 2 are performed, the signals generated by hybridization of two probes with one particular clone can often be separated into the component signals even if the result is expressed by a single kind of signal such as an autoradiogram based on radioisotope labeling, instead of the below-described multicolor probe. First, each probe can be identified if there is one "2" as described above even when the difference in signal intensities generated by each probe is small. In addition, each probe can be identified when there is a definite difference between the signals, even when there are two or more "2". For example, the sum of FORWARD ID (1111100) and REVERSE ID (11111111) becomes "22222211," indicating the hybridization of more than two probes. Here, we assume that these are strong and weak signals and can be distinguished. If we represent the strong and weak signals for the bit having 2 as the sum by S1 and W1, the above results may be expressed as FOR- WARD ID (S1, W1, S1, S1, S1, W1, 0, 0) and REVERSE ID (W1, S1, W1, W1, W1, S1, 1, 1). From these results, the FORWARD ID of the probe expressing the strong signal is 10111000, and the FORWARD ID of the probe expressing the weak signal is 01000100. Although three or more STS probes may be hybridized, the unnecessary secondary or tertiary screenings may be omitted when the correlation can be confirmed using the probe having the ID number thus isolated. Furthermore, the method of using two eight-bit ID numbers is equivalent to assigning one 16-bit ID number. Thus, the fidelity of the method of the present invention can be enhanced by using an additional bit for the minimally required bits. "Minimally required bits" means the number of bits (n) needed for assigning individual ID numbers to test samples in group A. For this purpose, additional bits are provided by adding a desired number of bits to the minimally required bits to produce a g-bit ID number.

In many cases in which two probes are assumed to correspond to one particular clone, the number of combinations of two STS probes assumed to interact can be narrowed by using additional bits. For example, if the addition of n bits is sufficient, the number of probe combinations can be reduced to ¼ to ¹⁄₁₆ of that when the screening is carried out with probes having an n-bit ID number when screenings 1 and 2 are performed after assigning an (n+2)-bit ID number to STS probes by using an additional two bits. The more bits added, the greater the reduction becomes. However, the necessary number of bits should be determined considering the frequency of correspondence of two probes to one clone since additional probe mixtures must be prepared in proportion to the additional bits.

(4) Another screening with a second series of oligonucleotide probes (such as reverse primers) will decrease the number of false-positive signals.

(5) Certain probes may hybridize with multiple clones if they contain multicopy sequences such as long and short repetitive sequences. This would interfere with determining the proper ID number. These repetitive sequences, if known, should be eliminated by performing a careful homology search in computer databases. In practice, a preliminary experiment should generally be performed to find and eliminate undesired STS probes prior to actual screening. When group A contains oligonucleotide probes having affinity to multicopy sequences such as long and short repetitive sequences, the identical reaction pattern for the same clone may be observed among different probe mixtures. Therefore, the oligonucleotides to be eliminated will be detected using this unique reaction pattern as a marker. In this invention, probes causing such a non-specific reaction are designated as bad background oligo-probes (BBO). The concepts of steps (1) through (5) can be used not only singly but also in proper combinations, assigning various choices for enhancing the fidelity of screening according to this invention.

The interacting combination of STS markers and genome library can be detected by reacting probe mixtures (group A) comprising labeled STS markers with genome libraries (group B) fixed on filters or DNA chips. Methods for fixing a genome library to filters are known. Although there are several tens of thousands to several hundreds of thousands of clones in each genome library, an efficient assay system can be constructed by using a high-density filter on which several thousand varieties of clones can be fixed. DNA chips are also useful for fixing DNA at a high density. Each clone of the genome library is separately fixed in a grid on the DNA chip and reacted with the mixture of fluorescence-labeled probes. The grid showing a positive hybridization reaction is then determined. The treating capability is remarkably enhanced as compared with the conventional method requiring one by one reaction by reacting the probe mixture with a highly cumulated library.

As described above, more correct results are obtained in the method for determining the correlation according to the present invention, when the number of test samples in group B correlated to those in group A is in a ratio of 1:1, or 1:many. This is because, in principle, only two kinds of data, positive "1" or negative "0," can be obtained when radioisotope labels are detected by autoradiography. When two or more probes detect one target, the correct ID number cannot be derived owing to the overlapped signals. However, the correct correlation will be found when a special labeling method is used as described below even with a many:1 correspondence. This method will be described with reference to an example for finding the correlation between STS probes and the genome library.

For example, STS probes are assigned many varieties of labeling to generate distinguishable signals. Such labeling is exemplified by that with fluorescence pigments of different fluorescence wavelengths and pigments having different colors. When all probes are labeled so as to give the same signal, it is difficult to distinguish the correspondence if many probes correspond to a particular clone (that is, a many:1 correspondence). However, when many probes have distinguishable different signals, it is possible to clarify which co-present probe reacts, enabling the separation of signals. For example, if two kinds of probes correspond to a single clone, a five-color labeling theoretically enables the identification of probes in 80% of the cases. In the present invention, such multilabeled probes enabling the determination of more correct correlation is designated multicolor probes.

It is also possible to minimize the number of ID numbers by using a multicolor probe because even though the identical ID number is assigned to different test samples, they can be distinguished by the difference in labeling. Using this characteristic, it is theoretically possible to reduce the number of varieties of mixtures (the number of reactions for establishing the correspondence) in proportion to the number of varieties of labeling. For example, when the identical ID number is assigned to five different probes using five varieties of labels, the number of mixtures will be reduced to ⅕.

By using the method for determining the interacting combination of the present invention, it is possible to efficiently perform not only genome analysis but also the screening of transcriptional regulatory agents and agonist compounds for the membrane receptor. These applications will be specifically described in the following.

The present invention can be applied to screening transcriptional regulators corresponding to target genes. The present invention allows simultaneous screening of the activity of candidate compounds in the transcriptional regulatory region corresponding to each of numerous target genes not to a single target. Transcriptional evaluation plasmids are prepared by inserting the structure formed by replacing the coding region of each gene with a reporter gene and linking it to the. transcriptional regulatory region localized upstream of its 5'-side. The transcriptional regulatory activity is then assayed by successively contacting said transformants with candidate compound mixtures. By transforming each transformant with many varieties of plasmid, conditions equivalent to those corresponding to the mixtures of test samples in group A can be constructed. By just screening each candidate compound using a few transformants, the correlation of candidate compounds having transcriptional regulatory activity with the transcriptional regulatory regions as their targets can be determined.

The present invention also enables the efficient screening of agonist compounds for membrane receptors with unknown functions as a part of the functional analysis of genes. The transcriptional signal at the final stage of the intracellular signal transduction is utilized for this screening. A considerable portion of the final transcriptional signal generated by membrane receptors is thought to be classified into the terminal cAMP responsive element (CRE) of the cAMP signal, or AP1, one of the terminal elements of the Ca signal. Cultured cells are co-transformed by transferring a translational evaluation plasmid in which a reporter gene is linked downstream of CRE or AP1 and another plasmid expressing membrane receptor with unknown functions. The agonist activity of candidate compounds can be determined by contacting candidate agonist compounds with this transformant to detect the expression of the reporter activity. In this case, a process equivalent to that for preparing test sample mixtures in group A of the present invention can be achieved by transferring many membrane receptor genes to the same cell. The correlation between candidate compounds having agonist activity and their targeting membrane receptors can be found by just screening each candidate compound using a few transformants. In this method, the correlation between receptors and agonists can be detected even with membrane receptors having unknown functions, provided they trigger the signal transduction mediated by CRE and AP1.

Epitope analysis of monoclonal antibodies can also be performed based on the present invention. Antigen fragments are first prepared as test samples in group A. For example, in the case of proteinaceous antigens, oligopeptide libraries comprising amino acid sequences shifted by several amino acids each from the terminus are synthesized and assigned ID numbers. Epitope analysis can be performed by identifying the correlation of these libraries with monoclonal antibodies as test samples in group B. For some macromolecular antigens, the correspondence to several hundreds of oligonucleotides might have to be examined. However, the application of the present invention enables clarifying the correlation with only a few assays.

BEST MODE FOR IMPLEMENTING THE INVENTION

The present invention will be described more specifically with reference to examples, but is not to be construed to be limited thereto.

EXAMPLE 1

Screening with the present invention was performed using 15,360 BAC clones [Gene 191 (1997), p69–79] and 126 STS markers (Tables 8 to 10). Each of the nucleotide sequences of STS markers and primers is available from dbSTS provided by NCBI and DDBJ Accession No. C75685–C75936. In this case, a seven-bit ID number was assigned to each of the 126 probes as shown in Tables 8 through 10. Eight mixtures of STS marker probes (FA, F1 through F7) were provided The mixture FA contained all 126 STS probes, and other mixtures contained 63 STS probes in arranged combinations.

To a reaction mixture (50 $\mu$l) containing 0.1 pmol each of 63 (or 126) STS marker oligonucleotides (forward amplimers) were added 31.5 $\mu$Ci (or 63 $\mu$Ci) of [$\gamma$-$^{32}$P]ATP (5,000 Ci/mmol, AA0018, Amersham), and one (or two) units of T4 polynucleotide kinase (Takara). The mixture was then incubated at 37° C. for 30 min. The unincorporated [$\gamma$-$^{32}$P]ATP was removed with a Sephadex G-50 spun-column. Approximately 50% of the $^{32}$P was incorporated. Prehybridization was performed at 55° C. for 12 h with a solution of 5×SSC, 5×Denhardt's, 0.5% SDS containing 0.1 mg/ml denatured salmon testes DNA (Sigma, D3159; average 200 bp), and 0.2 mg/ml denatured herring sperm DNA (Sigma D1626) (average<100 bp) which were fragmented by sonication. After the prehybridization, the labeled probes were added to the reaction mixture and incubated at 55° C. for 72 h. The final concentration of each probe was 0.005 pmol/ml. The filters were washed three times with 2×SSC and 0.5% SDS for 10 min at room temperature, followed by two washings for 30 min at 60° C., and finally washed with 0.1×SSC and 0.1% SDS for 10 min at room temperature. The filters were exposed against Fuji imaging plates for 72 h. The autoradiograms were obtained with a BAS 2000 Bio Imaging analyzer (Fuji Photo Film).

Each of these probe mixtures labeled with $^{32}$P by the above-described method was separately hybridized against five sets of high-density replica (HDR) filters, on which 3072 BAC clones were blotted. Hybridization signals were clearly observed in autoradiograms. The probe mixture FA containing all 126 probes detected 30 BAC clones on this particular HDR filter (a total of 104 clones for five separate HDR filters), whereas the seven other probe mixtures detected these same clones in different combinations. The hybridization signal patterns were examined by the method disclosed in the present specification. For example, BAC 66 was positive for probe mixtures F7, F5, F4, and F1, but negative for F6 and F3, resulting in the seven-bit pattern "1011011" (Tables 11 to 12). As a result, the correlation between BAC 66 and a specific STS probe, D11S1308 (Tables 8 to 10), was determined. In the same way, the seven-bit numbers of the remaining clones were determined, and the correlation was established with 48 specific STS probes. Among the 48 STS probes, two probes (STS7 and STS23) detected more clones than expected, a total of 23 BAC clones (eight and 15 clones, respectively). This is probably because these probes contain multicopy repetitive sequences, although these oligonucleotide probes were designed to be as unique as possible to prevent false-positive signals upon hybridization. In order to confirm the fidelity of the digital hybridization screening, the PCR analysis was performed, eliminating these 23 BAC clones. The method of PCR analysis will be described below.

PCR analysis was performed for 81 clones using forward and reverse amplimers designed for each of 46 STS marker probes selected by the above-described method. The results of PCR analysis together with DH screening data are shown in Tables 11 and 12. The PCR analysis indicated that 76 BAC clones were analyzable and five clones were not. Among these 76 BAC clones, 59 clones were confirmed to correlate with 37 specific STS markers. These results clearly indicate the high success rate (59/76=78%) for detecting the correlation between clones and STS markers.

TABLE 8

| | STS | FA | F7 | F6 | F5 | F4 | F3 | F2 | F1 |
|---|---|---|---|---|---|---|---|---|---|
| 1 | AFM067XD7 | 1 | 0 | 0 | 0 | 0 | 0 | 0 | 1 |
| 2 | AMF144XC3 | 1 | 0 | 0 | 0 | 0 | 0 | 1 | 0 |
| 3 | AMF207YF10 | 1 | 0 | 0 | 0 | 0 | 0 | 1 | 1 |
| 4 | AMF287ZD5 | 1 | 0 | 0 | 0 | 0 | 1 | 0 | 0 |
| 5 | AFM333ZD9 | 1 | 0 | 0 | 0 | 0 | 1 | 0 | 1 |
| 6 | AMFA083XE1 | 1 | 0 | 0 | 0 | 0 | 1 | 1 | 0 |
| 7 | AMFA106ZE1 | 1 | 0 | 0 | 0 | 0 | 1 | 1 | 1 |
| 8 | AMFA340ZG1 | 1 | 0 | 0 | 0 | 1 | 0 | 0 | 0 |
| 9 | CHLC.ATA27F01 | 1 | 0 | 0 | 0 | 1 | 0 | 0 | 1 |
| 10 | CHLC.GATAZ9C02 | 1 | 0 | 0 | 0 | 1 | 0 | 1 | 0 |
| 11 | CHLC.GATA29D01 | 1 | 0 | 0 | 0 | 1 | 0 | 1 | 1 |
| 12 | CHLC.GATA43F04 | 1 | 0 | 0 | 0 | 1 | 1 | 0 | 0 |
| 13 | CHLC.GATA45C03 | 1 | 0 | 0 | 0 | 1 | 1 | 0 | 1 |
| 14 | CHLC.GATA49E01 | 1 | 0 | 0 | 0 | 1 | 1 | 1 | 0 |
| 15 | CHLC.GATA71H10 | 1 | 0 | 0 | 0 | 1 | 1 | 1 | 1 |
| 16 | CHLC.GGAA3C07 | 1 | 0 | 0 | 1 | 0 | 0 | 0 | 0 |
| 17 | D21S1255 | 1 | 0 | 0 | 1 | 0 | 0 | 0 | 1 |
| 18 | D21S1256 | 1 | 0 | 0 | 1 | 0 | 0 | 1 | 0 |
| 19 | D21S1257 | 1 | 0 | 0 | 1 | 0 | 0 | 1 | 1 |
| 20 | D21S1258 | 1 | 0 | 0 | 1 | 0 | 1 | 0 | 0 |
| 21 | D21S1260 | 1 | 0 | 0 | 1 | 0 | 1 | 0 | 1 |
| 22 | D21S1425 | 1 | 0 | 0 | 1 | 0 | 1 | 1 | 0 |
| 23 | D21S1885 | 1 | 0 | 0 | 1 | 0 | 1 | 1 | 1 |
| 24 | D21S1909 | 1 | 0 | 0 | 1 | 1 | 0 | 0 | 0 |
| 25 | D21S1913 | 1 | 0 | 0 | 1 | 1 | 0 | 0 | 1 |
| 26 | D21S1914 | 1 | 0 | 0 | 1 | 1 | 0 | 1 | 0 |
| 27 | D21S1915 | 1 | 0 | 0 | 1 | 1 | 0 | 1 | 1 |
| 28 | D21S259 | 1 | 0 | 0 | 1 | 1 | 1 | 0 | 0 |
| 29 | S21S260 | 1 | 0 | 0 | 1 | 1 | 1 | 0 | 1 |
| 30 | D21S261 | 1 | 0 | 0 | 1 | 1 | 1 | 1 | 0 |
| 31 | D21S263 | 1 | 0 | 0 | 1 | 1 | 1 | 1 | 1 |
| 32 | D21S265 | 1 | 0 | 1 | 0 | 0 | 0 | 0 | 0 |
| 33 | D21S266 | 1 | 0 | 1 | 0 | 0 | 0 | 0 | 1 |
| 34 | D21S269 | 1 | 0 | 1 | 0 | 0 | 0 | 1 | 0 |
| 35 | D21S270 | 1 | 0 | 1 | 0 | 0 | 0 | 1 | 1 |
| 36 | IB2139 | 1 | 0 | 1 | 0 | 0 | 1 | 0 | 0 |
| 37 | NIB1480 | 1 | 0 | 1 | 0 | 0 | 1 | 0 | 1 |
| 38 | NIB1575 | 1 | 0 | 1 | 0 | 0 | 1 | 1 | 0 |
| 39 | NIB1972 | 1 | 0 | 1 | 0 | 0 | 1 | 1 | 1 |
| 40 | NIB517 | 1 | 0 | 1 | 0 | 1 | 0 | 0 | 0 |
| 41 | SGC30133 | 1 | 0 | 1 | 0 | 1 | 0 | 0 | 1 |
| 42 | SGC30487 | 1 | 0 | 1 | 0 | 1 | 0 | 1 | 0 |
| 43 | SGC30615 | 1 | 0 | 1 | 0 | 1 | 0 | 1 | 1 |

TABLE 9

| | STS | FA | F7 | F6 | F5 | F4 | F3 | F2 | F1 |
|---|---|---|---|---|---|---|---|---|---|
| 44 | SGC32169 | 1 | 0 | 1 | 0 | 1 | 1 | 0 | 0 |
| 45 | SGC35207 | 1 | 0 | 1 | 0 | 1 | 1 | 0 | 1 |
| 46 | SGC35308 | 1 | 0 | 1 | 0 | 1 | 1 | 1 | 0 |
| 47 | SGC35315 | 1 | 0 | 1 | 0 | 1 | 1 | 1 | 1 |
| 48 | WI-11321 | 1 | 0 | 1 | 1 | 0 | 0 | 0 | 0 |
| 49 | WI-11358 | 1 | 0 | 1 | 1 | 0 | 0 | 0 | 1 |
| 50 | WI-11417 | 1 | 0 | 1 | 1 | 0 | 0 | 1 | 0 |
| 51 | WI-11948 | 1 | 0 | 1 | 1 | 0 | 0 | 1 | 1 |
| 52 | WI-12452 | 1 | 0 | 1 | 1 | 0 | 1 | 0 | 0 |
| 53 | WI-13017 | 1 | 0 | 1 | 1 | 0 | 1 | 0 | 1 |
| 54 | WI-13322 | 1 | 0 | 1 | 1 | 0 | 1 | 1 | 0 |
| 55 | WI-13874 | 1 | 0 | 1 | 1 | 0 | 1 | 1 | 1 |
| 56 | WI-14954 | 1 | 0 | 1 | 1 | 1 | 0 | 0 | 0 |
| 57 | WI-16318 | 1 | 0 | 1 | 1 | 1 | 0 | 0 | 1 |
| 58 | WI-16888 | 1 | 0 | 1 | 1 | 1 | 0 | 1 | 0 |
| 59 | WI-16986 | 1 | 0 | 1 | 1 | 1 | 0 | 1 | 1 |
| 60 | WI-17090 | 1 | 0 | 1 | 1 | 1 | 1 | 0 | 0 |
| 61 | WI-17658 | 1 | 0 | 1 | 1 | 1 | 1 | 0 | 1 |
| 62 | WI-17664 | 1 | 0 | 1 | 1 | 1 | 1 | 1 | 0 |
| 63 | WI-17843 | 1 | 0 | 1 | 1 | 1 | 1 | 1 | 1 |
| 64 | WI-18279 | 1 | 1 | 0 | 0 | 0 | 0 | 0 | 0 |
| 65 | WI-18470 | 1 | 1 | 0 | 0 | 0 | 0 | 0 | 1 |
| 66 | WI-18695 | 1 | 1 | 0 | 0 | 0 | 0 | 1 | 0 |

TABLE 9-continued

| | STS | FA | F7 | F6 | F5 | F4 | F3 | F2 | F1 |
|---|---|---|---|---|---|---|---|---|---|
| 67 | WI-6909 | 1 | 1 | 0 | 0 | 0 | 0 | 1 | 1 |
| 68 | WI-7384 | 1 | 1 | 0 | 0 | 0 | 1 | 0 | 0 |
| 69 | WI-7555 | 1 | 1 | 0 | 0 | 0 | 1 | 0 | 1 |
| 70 | WI-7775 | 1 | 1 | 0 | 0 | 0 | 1 | 1 | 0 |
| 71 | WI-7805 | 1 | 1 | 0 | 0 | 0 | 1 | 1 | 1 |
| 72 | WI-7910 | 1 | 1 | 0 | 0 | 1 | 0 | 0 | 0 |
| 73 | WI-8007 | 1 | 1 | 0 | 0 | 1 | 0 | 0 | 1 |
| 74 | WI-8865 | 1 | 1 | 0 | 0 | 1 | 0 | 1 | 0 |
| 75 | WI-9091 | 1 | 1 | 0 | 0 | 1 | 0 | 1 | 1 |
| 76 | WI-9170 | 1 | 1 | 0 | 0 | 1 | 1 | 0 | 0 |
| 77 | WI-9545 | 1 | 1 | 0 | 0 | 1 | 1 | 0 | 1 |
| 78 | WI-9587 | 1 | 1 | 0 | 0 | 1 | 1 | 1 | 0 |
| 79 | D20S864 | 1 | 1 | 0 | 0 | 1 | 1 | 1 | 1 |
| 80 | FKBP | 1 | 1 | 0 | 1 | 0 | 0 | 0 | 0 |
| 81 | WI-8798 | 1 | 1 | 0 | 1 | 0 | 0 | 0 | 1 |
| 82 | D20S117 | 1 | 1 | 0 | 1 | 0 | 0 | 1 | 0 |
| 83 | D20SI99 | 1 | 1 | 0 | 1 | 0 | 0 | 1 | 1 |
| 84 | SGC30891 | 1 | 1 | 0 | 1 | 0 | 1 | 0 | 0 |
| 85 | SGC33911 | 1 | 1 | 0 | 1 | 0 | 1 | 0 | 1 |
| 86 | SGC35115 | 1 | 1 | 0 | 1 | 0 | 1 | 1 | 0 |

TABLE 10

| | STS | FA | F7 | F6 | F5 | F4 | F3 | F2 | F1 |
|---|---|---|---|---|---|---|---|---|---|
| 87 | WI-9706 | 1 | 1 | 0 | 1 | 0 | 1 | 1 | 1 |
| 88 | D20S171 | 1 | 1 | 0 | 1 | 1 | 0 | 0 | 0 |
| 89 | D20S173 | 1 | 1 | 0 | 1 | 1 | 0 | 0 | 1 |
| 90 | D11S1307 | 1 | 1 | 0 | 1 | 1 | 0 | 1 | 0 |
| 91 | D11S1308 | 1 | 1 | 0 | 1 | 1 | 0 | 1 | 1 |
| 92 | D11S1309 | 1 | 1 | 0 | 1 | 1 | 1 | 0 | 0 |
| 93 | DI1S1311 | 1 | 1 | 0 | 1 | 1 | 1 | 0 | 1 |
| 94 | D11S1312 | 1 | 1 | 0 | 1 | 1 | 1 | 1 | 0 |
| 95 | D11S1313 | 1 | 1 | 0 | 1 | 1 | 1 | 1 | 1 |
| 96 | D11S1315 | 1 | 1 | 1 | 0 | 0 | 0 | 0 | 0 |
| 97 | D11S1317 | 1 | 1 | 1 | 0 | 0 | 0 | 0 | 1 |
| 98 | D11S1319 | 1 | 1 | 1 | 0 | 0 | 0 | 1 | 0 |
| 99 | D11S1320 | 1 | 1 | 1 | 0 | 0 | 0 | 1 | 1 |
| 100 | D11S1321 | 1 | 1 | 1 | 0 | 0 | 1 | 0 | 0 |
| 101 | D11S1322 | 1 | 1 | 1 | 0 | 0 | 1 | 0 | 1 |
| 102 | D11S1323 | 1 | 1 | 1 | 0 | 0 | 1 | 1 | 0 |
| 103 | D11S1324 | 1 | 1 | 1 | 0 | 0 | 1 | 1 | 1 |
| 104 | D11S1325 | 1 | 1 | 1 | 0 | 1 | 0 | 0 | 0 |
| 105 | D11S1326 | 1 | 1 | 1 | 0 | 1 | 0 | 0 | 1 |
| 106 | D11S1327 | 1 | 1 | 1 | 0 | 1 | 0 | 1 | 0 |
| 107 | D11S1328 | 1 | 1 | 1 | 0 | 1 | 0 | 1 | 1 |
| 108 | D11S1329 | 1 | 1 | 1 | 0 | 1 | 1 | 0 | 0 |
| 109 | D11S1330 | 1 | 1 | 1 | 0 | 1 | 1 | 0 | 1 |
| 110 | D11S1331 | 1 | 1 | 1 | 0 | 1 | 1 | 1 | 0 |
| 111 | D11S1332 | 1 | 1 | 1 | 0 | 1 | 1 | 1 | 1 |
| 112 | D11S1333 | 1 | 1 | 1 | 1 | 0 | 0 | 0 | 0 |
| 113 | D11S1335 | 1 | 1 | 1 | 1 | 0 | 0 | 0 | 1 |
| 114 | D11S1336 | 1 | 1 | 1 | 1 | 0 | 0 | 1 | 0 |
| 115 | D11S1337 | 1 | 1 | 1 | 1 | 0 | 0 | 1 | 1 |
| 116 | D11S1339 | 1 | 1 | 1 | 1 | 0 | 1 | 0 | 0 |
| 117 | D11S1340 | 1 | 1 | 1 | 1 | 0 | 1 | 0 | 1 |
| 118 | D11S1341 | 1 | 1 | 1 | 1 | 0 | 1 | 1 | 0 |
| 119 | D11S1342 | 1 | 1 | 1 | 1 | 0 | 1 | 1 | 1 |
| 120 | E-22 | 1 | 1 | 1 | 1 | 1 | 0 | 0 | 0 |
| 121 | E-68 | 1 | 1 | 1 | 1 | 1 | 0 | 0 | 1 |
| 122 | E-86 | 1 | 1 | 1 | 1 | 1 | 0 | 1 | 0 |
| 123 | E-161 | 1 | 1 | 1 | 1 | 1 | 0 | 1 | 1 |
| 124 | E-218 | 1 | 1 | 1 | 1 | 1 | 1 | 0 | 0 |
| 125 | E-836 | 1 | 1 | 1 | 1 | 1 | 1 | 0 | 1 |
| 126 | E-877 | 1 | 1 | 1 | 1 | 1 | 1 | 1 | 0 |

TABLE 11

| clone | DH result | STS | PCR |
|---|---|---|---|
| 1 | 0011000 | 24 | P |
| 2 | 1111010 | 122 | P |

TABLE 11-continued

| clone | DH result | STS | PCR |
|---|---|---|---|
| 3 | 0010001 | 17 | P |
| 4 | 1011011 | 91 | P |
| 5 | 1011101 | 93 | P |
| 6 | 0001010 | 10 | P |
| 7 | 0101010 | 42 | P |
| 8 | 0011110 | 30 | P |
| 9 | 1001110 | 78 | P |
| 10 | 1111010 | 122 | N |
| 11 | 1001110 | 78 | N |
| 12 | 1001111 | 79 | — |
| 13 | 0111010 | 58 | — |
| 14 | 1111010 | 122 | P |
| 15 | 0110001 | 49 | P |
| 16 | 1111001 | 121 | P |
| 17 | 1100101 | 101 | P |
| 18 | 0111000 | 56 | P |
| 19 | 0000011 | 3 | P |
| 20 | 1101110 | 110 | P |
| 21 | 1011010 | 90 | P |
| 22 | 0111111 | 63 | P |
| 23 | 1101101 | 109 | P |
| 24 | 1011111 | 95 | P |
| 25 | 1101111 | 111 | P |
| 26 | 1000011 | 67 | P |
| 27 | 1101111 | 111 | N |
| 28 | 0111111 | 63 | N |
| 29 | 0000011 | 3 | N |
| 30 | 1000010 | 66 | N |
| 31 | 0000101 | 5 | — |
| 32 | 0000101 | 5 | — |
| 33 | 0011111 | 31 | — |
| 34 | 1111110 | 126 | P |
| 35 | 1000111 | 71 | P |
| 36 | 0010110 | 22 | P |
| 37 | 1000011 | 67 | P |
| 38 | 1111100 | 124 | P |
| 39 | 1011011 | 91 | P |
| 40 | 0111011 | 59 | P |
| 41 | 0000100 | 4 | P |

TABLE 12

| clone | DH result | STS | PCR |
|---|---|---|---|
| 42 | 1000100 | 68 | P |
| 43 | 1010101 | 85 | P |
| 44 | 1101111 | 111 | N |
| 45 | 1111001 | 121 | N |
| 46 | 1010111 | 87 | N |
| 47 | 0011011 | 27 | P |
| 48 | 0111000 | 56 | P |
| 49 | 1110000 | 112 | P |
| 50 | 1110000 | 112 | P |
| 51 | 0101010 | 42 | P |
| 52 | 1101111 | 111 | P |
| 53 | 0110001 | 49 | P |
| 54 | 0110110 | 54 | N |
| 55 | 1011101 | 93 | N |
| 56 | 1111111 | — | — |
| 57 | 0010000 | 16 | P |
| 58 | 0011011 | 27 | P |
| 59 | 1000111 | 71 | P |
| 60 | 0000110 | 6 | P |
| 61 | 1011101 | 93 | P |
| 62 | 1111110 | 126 | P |
| 63 | 0011110 | 30 | P |
| 64 | 1100100 | 100 | P |
| 65 | 1011111 | 95 | P |
| 66 | 1011011 | 91 | P |
| 67 | 1011001 | 89 | P |
| 68 | 1101011 | 107 | P |
| 69 | 0011011 | 27 | P |
| 70 | 0010110 | 22 | P |
| 71 | 0100011 | 35 | P |

TABLE 12-continued

| clone | DH result | STS | PCR |
|---|---|---|---|
| 72 | 0000011 | 3 | P |
| 73 | 1000100 | 68 | P |
| 74 | 1101101 | 109 | P |
| 75 | 1000111 | 71 | P |
| 76 | 1101111 | 111 | P |
| 77 | 1111010 | 122 | N |
| 78 | 1010111 | 87 | N |
| 79 | 0101101 | 45 | N |
| 80 | 1010111 | 87 | N |
| 81 | 1101010 | 106 | N |

P: PCR positive
N: PCR negative
—: not informative

EXAMPLE 2

Oligonucleotide probes corresponding to human genomic repetitive sequences were detected in the five-bit digital hybridization method. Oligonucleotide probes having affinity for the repetitive sequences tend to detect extremely large numbers of clones besides the desired ones, complicating the analysis and interfering with the correct interpretation of results due to the many: 1 correlation between groups A and B. Therefore, the following example will describe how such undesirable oligonucleotide probes can be selected and eliminated as a more preferable embodiment of the present invention.

The comprehensive isolation of BAC clones on chromosome 8 was attempted using the digital hybridization screening method with 1014 expressed sequence tags (ESTs) mapped on chromosome 8 as probes. Either partner of a pair of oligonucleotide primers (forward and reverse) for PCR amplification of each EST marker was used as a probe. Nucleotide sequences of primers were selected from those registered in databases such as GDB. These nucleotide sequences should ideally be designed based on a single-copy sequence. In practice, however, they may often contain oligonucleotides derived from human genomic repetitive sequences. This results in the undesirable hybridization with BAC clones not corresponding to the original ESTs. In particular, when the frequency of the repetitive sequence from which the said oligonucleotide is derived is high on the genome, far more clones than desired will be selected as positive clones. Such a situation may greatly impede the performance of digital hybridization screening on a large scale. Therefore, digital hybridization screening was performed on a small scale before comprehensive screening was performed on a large scale.

First, 33 probe mixtures were prepared by dividing 1014 ESTs into portions of 31 ESTs each. Each probe mixture was labeled with $^{32}$P in a similar manner as described in Example 1. Colony hybridization was then performed using the above-described labeled probe mixtures against filters blotted with 6114 BAC clones (equivalent to approximately 0.2 genome). Screening the number of clones equivalent to 0.2 genome with 31 probes is theoretically expected to generate about six positive signals on average. However, screening with probe mixtures containing oligonucleotide probes derived from the repetitive sequences detected several tens to several hundreds of positive clones. Out of 33 sets of probe mixtures, five were found to contain oligonucleotide probes presumably derived from repetitive sequences. Therefore, the 31 oligonucleotide probes comprising these sets were specified by assigning a five-bit ID number to each probe, and the digital hybridization was performed. Partial results are shown in Table 13.

TABLE 13

| Original No. | name | M1 | M2 | M3 | M4 | M5 |
|---|---|---|---|---|---|---|
| 1 | 447 | StSG2728 | 0 | 0 | 0 | 0 | 1 |
| 2 | 450 | StSG2865 | 0 | 0 | 0 | 1 | 0 |
| 3 | 476 | StSG4053 | 0 | 0 | 0 | 1 | 1 |
| 4 | 492 | StSG4887 | 0 | 0 | 1 | 0 | 0 |
| 5 | 505 | StSG8247 | 0 | 0 | 1 | 0 | 1 |
| 6 | 521 | StSG8815 | 0 | 0 | 1 | 1 | 0 |
| 7 | 526 | StSG8968 | 0 | 0 | 1 | 1 | 1 |
| 8 | 584 | TIGR-A004G12 | 0 | 1 | 0 | 0 | 0 |
| 9 | 661 | TIGR-A008B17 | 0 | 1 | 0 | 0 | 1 |
| 10 | 664 | TIGR-A008N08 | 0 | 1 | 0 | 1 | 0 |
| 11 | 673 | TIGR-A008X11 | 0 | 1 | 0 | 1 | 1 |
| 12 | 675 | TIGR-A008Z29 | 0 | 1 | 1 | 0 | 0 |
| 13 | 676 | TIGR-A008Z39 | 0 | 1 | 1 | 0 | 1 |
| 14 | 705 | WI-11650 | 0 | 1 | 1 | 1 | 0 |
| 15 | 711 | WI-11745 | 0 | 1 | 1 | 1 | 1 |
| 16 | 715 | WI-11819 | 1 | 0 | 0 | 0 | 0 |
| 17 | 717 | WI-11882 | 1 | 0 | 0 | 0 | 1 |
| 18 | 721 | WI-12131 | 1 | 0 | 0 | 1 | 0 |
| 19 | 725 | WI-1243 | 1 | 0 | 0 | 1 | 1 |
| 20 | 727 | WI-12556 | 1 | 0 | 1 | 0 | 0 |
| 21 | 740 | WI-1310 | 1 | 0 | 1 | 0 | 1 |
| 22 | 759 | WI-14143 | 1 | 0 | 1 | 1 | 0 |
| 23 | 762 | WI-14186 | 1 | 0 | 1 | 1 | 1 |
| 24 | 778 | WI-15041 | 1 | 1 | 0 | 0 | 0 |
| 25 | 786 | WI-15306 | 1 | 1 | 0 | 0 | 1 |
| 26 | 797 | WI-15914 | 1 | 1 | 0 | 1 | 0 |
| 27 | 801 | WI-16152 | 1 | 1 | 0 | 1 | 1 |
| 28 | 802 | WI-16182 | 1 | 1 | 1 | 0 | 0 |
| 29 | 810 | WI-16696 | 1 | 1 | 1 | 0 | 1 |
| 30 | 816 | WI-16842 | 1 | 1 | 1 | 1 | 0 |
| 31 | 840 | WI-17906 | 1 | 1 | 1 | 1 | 1 |

Table shows five-bit ID numbers assigned to 31 probes in the 19th set which contained oligonucleotide probes presumably derived from the repetitive sequences. Probe mixtures M1 to M5 were prepared based on Table 13. Using each of these probe mixtures, colony hybridization was performed against identical filters blotted with each clone. Numerous clones were detected in the same pattern with M2 and M5. Therefore, the probe 661 (TGGR-A008B17) assigned ID number "01001" was determined to be derived from the repetitive sequences. The reaction pattern was then examined using probe mixtures from which only 661 (TGGR-A008B17) was eliminated. Elimination of the oligonucleotide probe which was judged to be derived from the repetitive sequences and to hybridize with many clones resulted in clearer patterns.

In a similar manner, oligonucleotide probes contained in other probe mixtures and presumably derived from the repetitive sequences were also detected. Finally, out of 1014 ESTs, five oligonucleotide probes derived from the repetitive sequences were detected and eliminated. The remaining 1009 ESTs were used for digital hybridization screening on a large scale.

Furthermore, 377 STS probes, from which oligonucleotide probes derived from the repetitive sequences were eliminated by a similar five-bit digital hybridization method as that for EST, were used to screen BAC clones (100,000 clones) on chromosome 7 too. A total of 1,386 STS probes and EST probes was divided into groups of 495, 490, and 401 to form three sets of probe mixtures.

With large-scale screening using combinations of EST probes and STS probes, about 4,300 out of 100,000 BAC clones could be rapidly screened as positive.

Next, these 4,300 clones were subcloned to generate sublibraries, and a more detailed correlation between each probe and the BAC libraries was made by performing an eight-bit digital hybridization screening. Some 1187 varieties of STS probes or EST probes were used for the digital hybridization.

Oligonucleotides designed based on the 1,187 different STS or EST sequences as probes were divided into five mixtures (comprising 236 to 238 probes). With these probe mixtures, eight-bit digital hybridization screening was performed against a sublibrary comprising about 4,300 BAC clones derived from chromosome 8 and previously screened. Each probe was assigned a FORWARD ID and a REVERSE ID, that is, specified by assigning two series of ID numbers such that the sum of FORWARD ID and REVERSE ID becomes (11111111). Therefore, each screening was performed using eight probe mixtures for FORWARD, eight probe mixtures for REVERSE, and one mixture containing all probes, a total of 17 probe mixtures. If the sum of ID numbers derived from results obtained by both FORWARD and REVERSE mixtures is (11111111), one particular kind of probe hybridized with the BAC clone and the correct result was obtained for the individual clone. After five screenings, one or more BAC clones could be correlated to the total of 670 varieties of STS (or EST). It was presumed that about 70 varieties of STSs (or ESTs) have STSs or ESTs extremely dose to each other, and two or more kinds of STS probes (or EST probes) hybridize with one particular BAC clone. As to the remaining 450 kinds of STS (or EST), it was assumed that no corresponding BAC clone was present in the sublibrary.

Thirty man-days was required to screen with 670 varieties of STS (or EST) probes. Such a speedy identification of BAC clones corresponding to 670 varieties of STS probes is impossible for the conventional method wherein correlations are determined one after another for all combinations of probes and clones.

EXAMPLE 3

Application of the present invention to screening transcriptional regulatory agents will be more specifically described with reference to screening agonist compounds against transcription factors belonging to the steroid receptor superfamily.

The following 10 varieties of transcription factors belonging to the steroid receptor superfamily are chosen:

glucocorticoid receptor α, progesterone receptor α, androgen receptor α, estrogen receptor α, retinoic acid receptor α1, retinoid X receptor α, thyroid hormone receptor α1, vitamin D3 receptor, peroxisome proliferator activated receptor γ1, and hepatocyte nuclear factor 4-β1.

The correlation between transcription factors corresponding to these receptors and agonist compounds will be determined using the present invention. CV-1 cells are used as cultured cells to be transformed. CV-1 cells cultured in a DMEM medium supplemented with 10% fetal bovine serum were washed twice with PBS(−), trypsin/EDTA was added to them, and cells were incubated at 37° C. for 5 min. Cells were then suspended in the added medium and centrifuged. Sedimented cells are resuspended in the added medium so that the cell density becomes $2 \times 10^5$ cells/2.5 ml. Cells are inoculated 2.5 ml/well onto six-well plates and cultured in a $CO_2$ incubator (37° C., 5% $CO_2$) for 18 to 24 h.

CV-1 cells thus seeded are transformed by transcriptional evaluation plasmids. Transcriptional evaluation plasmids have a structure wherein the luciferase gene is linked downstream of each transcription factor. In this example, plasmids harboring the above-described 10 varieties of transcription factors are mixed as shown in Table 14 and used for transformation. In this table, the line for each plasmid has a four-bit ID number, F4 to F1, and the F4 to F1 column indicates the presence ("1") or absence ("0") of plasmid in each mixture. Mixture FA contains all plasmids. When the use of this mixture fails to detect signals indicating the correlation between plasmid and candidate compounds as the transcriptional regulatory factor, the transcriptional regulatory activity may not exist for all compounds tested or operational procedures may have gone awry.

TABLE 14

| Transcription factor | FA | F4 | F3 | F2 | F1 |
| --- | --- | --- | --- | --- | --- |
| 1 Glucocorticoid receptor α | 1 | 0 | 0 | 0 | 1 |
| 2 Progesterone receptor α | 1 | 0 | 0 | 1 | 0 |
| 3 Androgen receptor α | 1 | 0 | 0 | 1 | 1 |
| 4 Estrogen receptor α | 1 | 0 | 1 | 0 | 0 |
| 5 Retinoic acid receptor α1 | 1 | 0 | 1 | 0 | 1 |
| 6 Retinoid X receptor α | 1 | 0 | 1 | 1 | 0 |
| 7 Thyroid hormone receptor α1 | 1 | 0 | 1 | 1 | 1 |
| 8 Vitamin D3 receptor | 1 | 1 | 0 | 0 | 0 |
| 9 Peroxisome poliferator activated receptor γ1 | 1 | 1 | 0 | 1 | 0 |
| 10 Hepatocyte nuclear factor 4-α1 | 1 | 1 | 0 | 1 | 1 |

Each plasmid is used in the amount of 0.3 μg diluted in 150 l of Opti-MEM. Lipofect AMINE reagent (7.0 μl) is added to a solution containing this evaluation plasmid, and the mixture is incubated at room temperature for 15 to 45 min. After incubation, the plasmid solution is further washed twice with PBS (−) (1 ml), and then added to CV-1 cells. After the cells are incubated in a $CO_2$ incubator for 4 h, the transformation solution is removed, trypsin/EDTA (200 μl) is added, and the cell suspension is allowed to stand at 37° C. for 5 min. After DMEM medium (containing no phenol red) supplemented with 10% active charcoal-treated fetal calf serum (1 ml) is added, cells are transferred into a centrifuge tube. Cells are recovered by centrifugation at 1,000 rpm for 3 min, resuspended so that the cell density becomes $1.6 \times 10^4$ cells/50 μl, and inoculated 50 μl/well onto a 96-well plate. After incubation in a $CO_2$ incubator for 1 h or longer, a solution of a candidate compound at a proper concentration is added 50 μl/well onto a 96-well plate. After the addition, cells are cultured in a $CO_2$ incubator for 40 to 48 h. The transcriptional regulatory activity is then confirmed by luciferase assay in the following procedures.

After the culture medium is removed from the 96-well plate, wells are washed with PBS(−) (100 μl). To the washed cells was added 1×Passive lysis buffer (Promega) (20 μl), and the cell suspension was incubated at room temperature for more than 15 min to lyze cells. The cell lysis solution thus obtained as the test sample was made luminescent, and the luminescence intensity was measured with a luminometer such as MLX (DYNAX Technologies).

INDUSTRIAL APPLICABILITY

In the present invention, when test samples in group A and those in group B are correlated so as to interact, a method for determining said correlation is provided. Reaction procedures for screening can be remarkably reduced in the present invention by utilizing test samples in group A mixed according to the principle of binary notation. Theoretically, the number of screenings decreases when there are seven or more test samples in group A, and as the number of test samples in group A increases, the reduction becomes greater.

The field of application of the method for determining the correlation based on the present invention is exemplified by mapping of STS and EST to a genomic library. These procedures are just the procedures for determining the correlation of group A (i.e., STS) and group B (i.e., genome library) based on the hybridization of both groups. Furthermore, because of the enormously large scale of both groups, the effect of the present invention to reduce the number of screenings is highly promissing. Through the increased efficiency of screening, the present invention will greatly contribute to promoting large-scale genome analysis including the Human Genome Project.

What is claimed is:

1. A method for determining a physical, chemical, or biological correlation between a combination of test samples constituting groups A and B, comprising:

providing m test samples Ai in group A and x test samples Bj in group B;

assigning a random g-bit binary ID number to each of said test samples Ai in group A;

mixing said test samples Ai in group A having "1" for the first bit of said randomly assigned ID number in binary notation to make a mixture C1, and similarly mixing test samples Ai in group A having "1" for the k-th bit of said assigned ID number to make a mixture Ck, thus obtaining g varieties of mixtures comprising mixtures C1 through Cg;

detecting any interaction between each of said g varieties of mixtures C1 through Cg with test samples Bj in group B;

determining g-bit binary numbers having "1" or "0" for the k-th bit, including assigning a "1" when the interaction is detected between each mixture C1 through Cg and test samples Bj in group B and assigning a "0" when no interaction is detected; and determining the correlation between test sample Ai in group A and test sample Bj in group B by referring test sample Ai in group A to the corresponding binary number obtained in said determining g-bit binary numbers step, wherein:

$2^{n-1} = <m = <2^n - 1$;

$2^{n-1} = <m = <2^n - 1$;

m>=3;

n>=2;

3=<i=<m;

1=<j=<x;

n=<g;

1=<k=<g; and m, n, and x are integers.

2. The method of claim 1, wherein the correlation between test samples is based on the interaction between test samples constituting group A and group B.

3. The method of claim 2, wherein the correlation based on the interaction between test samples has a ratio of 1:1 or 1:many.

4. The method of claim 1, wherein g is equal to n.

5. The method of claim 4, wherein said assigning a g-bit ID number step comprises assigning each test sample in group A an individual ID number up to $2^n - 1$.

6. The method claim 1, wherein said method comprises steps for detecting the interaction between mixtures obtained by mixing all test samples in group A and test sample Bj in group B.

7. The method of claim 1, wherein said test samples Ai comprise an oligonucleotide and said test samples Bj comprise DNA.

8. The method of claim 7, wherein:

said test samples Ai comprise STS markers; and said test samples Bj comprise genome libraries.

9. The method of claim 1, wherein said test samples Ai comprise a transcriptional evaluation plasmid and said test samples Bj comprise a candidate transcriptional regulator.

10. The method of claim 1, wherein said test samples Ai comprise a membrane receptor and said test samples Bj comprise an agonist compound.

11. The method of claim 1, wherein said test samples Ai comprise an antigen fragment and said test samples Bj comprise a monoclonal antibody.

12. A method for determining a combination of test samples out of those constituting groups A and B and correlating them physically, chemically or biologically, wherein said method comprises:

assigning random ID numbers of more than two series to one test sample in group A;

mixing said test samples Ai in group A having "1" for the first bit of said randomly assigned ID number in binary notation to make a mixture C1, and similarly mixing test samples Ai in group A having "1" for the k-th bit of said assigned ID number to make a mixture Ck, thus obtaining g varieties of mixtures comprising mixtures C1 through Cg;

detecting any interaction between each of said g varieties of mixtures C1 through Cg with test samples Bj in group B;

determining g-bit binary numbers having "1" or "0" for the k-th bit, including assigning a "1" when the interaction is detected between each mixture C1 through Cg and test samples Bj in group B and assigning a "0" when no interaction is detected; and determining the correlation between test sample Ai in group A and test sample Bj in group B by referring test sample Ai in group A to the corresponding binary number obtained in said determining g-bit binary numbers step, wherein said mixing, detecting, determining g-bit binary numbers, and determining the correlation steps are performed for each series of the randomly assigned ID numbers.

13. A method for determining a physical, chemical, or biological correlation between test samples Ai from a group A and test samples Bj from a group B, comprising:

assigning a respective random identification number to each of said test samples Ai;

mixing each of said plurality of test samples Ai according to a randomly selected common digit in said randomly assigned respective identification number to yield a plurality of common digit mixtures of test samples Ai;

allowing each of said test samples Bj to interact with each of said plurality of common digit mixtures of test samples Ai to yield a plurality of interactions; and detecting each of said plurality of interactions; and determining said correlation between said test samples Bj and said test samples Ai based upon said detected interactions.

14. The method of claim 13, wherein said respective identification number is a binary number.

15. The method of claim 13, wherein said allowing step comprises mixing each of said test samples Bj with each of said plurality of common digit mixtures of test samples Ai.

16. The method of claim 13, wherein said mixing step comprises fixing each of said plurality of test samples Ai according to a common digit in an area of a solid support.

17. The method of claim 13, wherein said test samples Ai comprise an oligonucleotide and said test samples Bj comprise DNA.

* * * * *